United States Patent [19]

Monn

[11] Patent Number: 5,591,867

[45] Date of Patent: Jan. 7, 1997

[54] SYNTHESIS OF KAINIC ACID

[75] Inventor: James A. Monn, Indianapolis, Ind.

[73] Assignee: Eli Lilly and Company, Indianapolis, Ind.

[21] Appl. No.: 550,422

[22] Filed: Oct. 30, 1995

Related U.S. Application Data

[62] Division of Ser. No. 231,543, Apr. 22, 1994, Pat. No. 5,486,620, which is a division of Ser. No. 56,687, Apr. 30, 1993, Pat. No. 5,352,799, which is a continuation-in-part of Ser. No. 985,986, Dec. 4, 1992, Pat. No. 5,319,095.

[51] Int. Cl.$^6$ .................................................. C07D 513/16
[52] U.S. Cl. .......................................... 548/532; 548/533
[58] Field of Search ..................................... 548/532, 533

[56] References Cited

FOREIGN PATENT DOCUMENTS 795750  5/1958  United Kingdom ................... 548/532

OTHER PUBLICATIONS

Oppolzer and Andres, "A Total Synthesis of α–Kainic Acid by an Intramolecular Ene Reaction", *Helv. Chim. Acta*, 62, p. 2282 (1979).

Potts, Choudhury, and Westby, "Bridgehead Nitrogen Systems.X. Cycloadditions with Thiazolium N–Ylides[1]", *J. Org. Chem.*, 41, p. 187 (1976).

Kraus and Nagy, "The synthesis of amino acids by 1,3–dipolar cycloadditions of azomethine ylides", *Tetrahedron*, 41, p. 3537 (1985).

Reetz, Kyung, and Hullman, "Ch$_3$Li/TiCl$_4$: A non–basic and highly selective Grignard analogue", *Tetrahedron*, 42, p. 2931 (1986).

Carlsen, Katsuki, Martin, and Sharpless, "A Greatly Improved Procedure for Ruthenium Tetraoxide Catalyzed Oxidations of Organic Compounds", *J. Org. Chem.*, 46, p. 3936 (1981).

Hibino, Okazoe, Takai, and Nozaki, "carbonyl methylenation of easily enolizable ketones", *Tetr. Lett.*, 26, p. 5579 (1985).

Takano, Sugihara, Satoh, and Ogasawara, "Enantioselective Synthesis of (–)-Kainic Acid", *J. Am. Chem. Soc.*, 110, p. 6467 (1988).

Husinec, Porter, Roberts, and Strachan, "Some Approaches to the Synthesis of Kainic Acid", *J. Chem. Soc., Perkin Trans. I*, p. 2517 (1984).

Husinec, Porter, and Strachan, "Approaches to the synthesis of kainic acid. A study of the synthesis of some 4,5–dihydro–1,2,3–triazoles", *Coll. Czech. Chem. Comm.*, 52, p. 207 (1987).

Murakami, Hasegawa, Hayashi, and Ito, "Synthesis of (±)–a–Allokainic Acid via the Zinc Acetate Catalyzed Cyclization of γ–Isocyano Silyl Enolates", *J. Org. Chem.*, 56, p. 7356 (1991).

Takano, Inomata, and Ogasawara, "A New Enantiospecific Route to (−)–Kainic Acid via the Intramolecular Pauson–Khand Reaction", *J. Chem. Soc., Chem. Comm.*, p. 169 (1992).

Green T., Protective Groups in Organic Synthesis, John Wiley and Sons, Inc., New York, 1981, pp. 218–222.

Patent Abstracts of Japan, vol. 12, 301 (C–521), 16 Aug., 1988 and JP–A–63072689.

Patent Abstracts of Japan, vol. 12, 33 (C–472), 30 Jan. 1988 and JP–A–62181286.

*Tetrahedron Letters*, 31, 47, p. 6877, 1990, 'Synthesis of alpha–kainic acid and alpha–allokainic acid by Pd(o)mediated olefin insertion–carbonylation reaction'.

*Tetrahedron Letters*, 32, 19, 1991, pp. 2137–2140 'An efficient preparation of 3–azabicyclo [3.3.0] –oct–5–en–7–ones from propargyl alcohol–cobalt complexes via Nicholas reaction with amidic nitrogen nucleophiles followed by Pauson–Khand cyclisation'.

*Tetrahedron Letters*, 34, 21, 1993, pp. 3435–3438 'A total synthesis of (–)–alpha–kainic acid by the Pauson–Khand reaction'.

*Tetrahedron*, 46, 20, 1990, pp. 7263–7282, 'Enantioselective Kainoid synthesis by cobalt–mediated cyclisation of an amino–acid derivative'.

Patent Abstracts of Japan, vol. 14, No. 137 (C–0702) Mar. 15, 1990 and JP–A–2011566.

*Database WPI*, Derwent publications Ltd. AN 93–299604 and JP–A–5 213 871, 24 Aug. 1993.

*Primary Examiner*—Jacqueline Haley
*Attorney, Agent, or Firm*—Martin A. Hay

[57] ABSTRACT

This invention provides a process for preparing kainic acid and provides intermediates in the synthesis thereof.

21 Claims, No Drawings

SYNTHESIS OF KAINIC ACID

CROSS REFERENCE

This application is a division, of application Ser. No. 08/231,543, filed on Apr. 22, 1994, now U.S. Pat. No. 5,486,620, which is a division of application Ser. No. 08/056,687, filed on Apr. 30, 1993, now U.S. Pat. No. 5,352,799, which is a continuation-in-part of application Ser. No. 07/985,986, filed on Dec. 4, 1992, now U.S. Pat. No. 5,319,095.

BACKGROUND OF THE INVENTION

The role of excitatory amino acids (EAA), such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. The excitatory amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connections during development and changes in the efficiency of synaptic transmission throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, perinatal hypoxia, cardiac arrest, hypoglyemic neuronal damage, ocular damage and retinopathy, and idiopathic and drug-induced Parkinson's Disease. Other neurological conditions, that are caused by glutamate dysfunction, may require neuromodulation. These other neurological conditions include muscular spasms, migraine headaches, urinary incontinence, psychosis, opiate tolerance and withdrawal, anxiety, emesis, brain edema, chronic pain, convulsions, and tardive dyskinesia. The use of a neuroprotective agent, such as an EAA receptor antagonist, is believed to be useful in treating these disorders and/or reducing the amount of neurological damage associated with these disorders.

The present invention is directed to a process for the preparation of an ionotropic excitatory amino acid receptor agonist, kainic acid (KA). Kainic acid is a necessary research tool for studying the pharmacology of the kainic acid receptor. McGeer, Olney, and McGeer, Kainic Acid as a Tool in Neurobiology, Raven Press, N.Y., 1978.

This invention provides a novel process for preparing kainic acid. The present process is shorter than the prior processes, comprising fewer chemical steps and a minimum number of purifications. The present process is also more efficient resulting in about 10% overall yield for all chemical reactions and purifications. The present process is also amenable to large-scale synthesis of kainic acid.

SUMMARY OF THE INVENTION

The present invention provides processes for the synthesis of kainic acid. More specifically, the present invention is directed to a process for preparing a compound of the formula

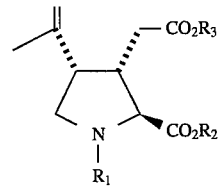

wherein $R_1$ is hydrogen, acyl, alkoxycarbonyl, or arylalkoxycarbonyl;

$R_2$ is hydrogen, $C_1$–$C_6$ alkyl, aryl, or arylalkyl; and $R_3$ is hydrogen, $C_1$–$C_6$ alkyl, aryl, or arylalkyl.

The present invention also provides processes for the preparation of intermediates that are useful for the synthesis of kainic acid. More specifically, the present invention provides processes for preparing a compound of the formula

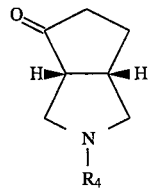

wherein $R_4$ is hydrogen, acyl, alkoxycarbonyl, or arylalkoxycarbonyl; and $R_5$ is hydrogen, $C_1$–$C_6$ alkyl, aryl, or arylalkyl. The present invention also provides processes for preparing a compound of the formula

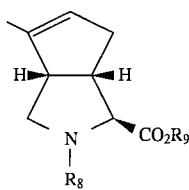

IV wherein
$R_8$ is acyl, alkoxycarbonyl, or arylalkoxycarbonyl; and
$R_9$ is $C_1$–$C_6$ alkyl, aryl, or arylalkyl.

The present invention also relates to compounds that are useful in the preparation of kainic acid. More specifically, the present invention relates to a compound of the formula

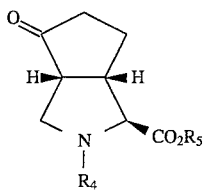

II wherein
$R_4$ is hydrogen, acyl, alkoxycarbonyl, or arylalkoxycarbonyl; and
$R_5$ is hydrogen, $C_1$–$C_6$ alkyl, aryl, or arylalkyl.

Another aspect of the present invention is a compound of the formula

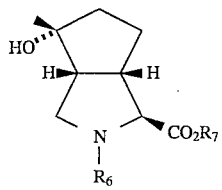

III wherein
$R_6$ is hydrogen, acyl, alkoxycarbonyl, or arylalkoxycarbonyl; and
$R_7$ is hydrogen, $C_1$–$C_6$ alkyl, aryl, or arylalkyl.

A further aspect of the present invention relates to the compounds of the formula

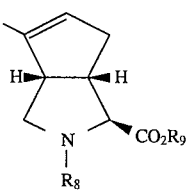

IV wherein
$R_8$ is hydrogen, acyl, alkoxycarbonyl, or arylalkoxycarbonyl; and
$R_9$ is hydrogen, $C_1$–$C_6$ alkyl, aryl, or arylalkyl.

Another aspect of the present invention is a compound of the formula

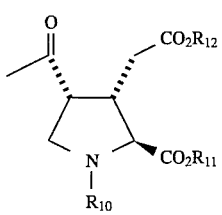

V wherein
$R_{10}$ is hydrogen, acyl, alkoxycarbonyl, or arylalkoxycarbonyl;
$R_{11}$ is hydrogen, $C_1$–$C_6$ alkyl, aryl, or arylalkyl; and
$R_{12}$ is hydrogen, $C_1$–$C_6$ alkyl, aryl, or arylalkyl;
provided that $R_{10}$, $R_{11}$, and $R_{12}$ are not all hydrogen.

Another aspect of the present invention is a compound of the formula

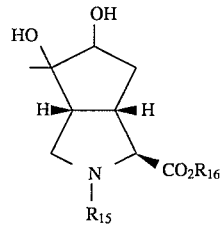

VIII wherein
$R_{15}$ is hydrogen, acyl, alkoxycarbonyl, or arylalkoxycarbonyl; and
$R_{16}$ is hydrogen, $C_1$–$C_6$ alkyl, aryl, or arylalkyl.

Another aspect of the present invention is a compound of the formula

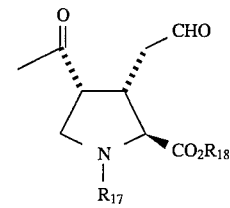

IX wherein
$R_{17}$ is hydrogen, acyl, alkoxycarbonyl, or arylalkoxycarbonyl; and
$R_{18}$ is hydrogen, $C_1$–$C_6$ alkyl, aryl, or arylalkyl.

DETAILED DESCRIPTION OF THE INVENTION

In the above formula, the term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, isobutyl, sec-butyl, t-butyl, n-pentyl, isopentyl, n-hexyl, 2-methylpentyl, and the like. The preferred $C_1$–$C_6$ alkyl groups are methyl and ethyl. The term "$C_1$–$C_6$ alkyl" includes within it the term "$C_1$–$C_4$ alkyl". Typical $C_1$–$C_4$ alkyl groups include methyl, ethyl, n-propyl, isopropyl, n-butyl, isobutyl, sec-butyl, and t-butyl. The preferred $C_1$–$C_4$ alkyl groups are methyl and ethyl.

The term "aryl" represents an aromatic group, including phenyl and naphthyl, or a heteroaromatic group, including furanyl, pyrrolyl, imidazolyl, and pyridinyl, substituted by one or more of the following: hydrogen, hydroxy, fluoro, chloro, bromo, iodo, cyano, nitro, $C_1$–$C_6$ alkyl, $C_1$–$C_4$ alkoxy, or trifluoromethyl. Typical aryl groups include phenyl, naphthyl, 2-pyridinyl, 2-imidazolyl, 4-chlorophenyl, 2,6-dichloropyhenyl, 4-bromophenyl, 4-hydroxyphenyl, 4-methylphenyl, 4-methoxyphenyl, 4-fluorophenyl, 2-bromophenyl, 2,4-diiodophenyl, 4-cyanophenyl, 2,4-dinitrophenyl, 4-ethylphenyl, 4-ethoxyphenyl, 4-trifluoromethylphenyl, 4-methylpyridin-2-yl, 4-methoxypyridin-2-yl, 3-fluoropyridin-2-yl, 4-cyanopyridin-2-yl, 4-trifluoromethylpyridin-2-yl, 4-methylimidazol-2-yl, 4,5-dimethylimidazol-2-yl, 4-methylfuran-2-yl, 5-methylfuran-2-yl, 4-methylpyrrol-2yl, and the like.

The term "$C_1$–$C_4$ alkoxy" represents groups such as methoxy, ethoxy, n-propoxy, isopropoxy, n-butoxy, t-butoxy, and the like groups.

The term "arylalkyl" represents a $C_1$–$C_4$ alkyl group bearing an aryl group. Representatives of this group include benzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl)methyl, (4-trifluoromethylphenyl)methyl, (4-methylpyridin-2-yl)methyl, (2,4-dinitrophenyl)methyl, (4,5-dimethylimidazol-2-yl)methyl, (4-methoxypyridin-2-yl)methyl, and the like groups. The preferred arylalkyl group is benzyl.

The term "alkoxycarbonyl" means a carboxyl group having a $C_1$–$C_6$ alkyl group attached to the carbonyl carbon through an oxygen atom. Representatives of this group include methoxycarbonyl, ethoxycarbonyl, n-propoxycarbonyl, n-butoxycarbonyl, t-butoxycarbonyl, and the like. The preferred alkoxycarbonyl group is methoxycarbonyl.

The term "arylalkoxycarbonyl" represents a carboxyl group having an arylalkyl group attached to the carbonyl carbon through an oxygen atom. Representatives of this group include benzyloxycarbonyl, 2-phenylethoxycarbonyl, 3-phenylpropoxycarbonyl, and the like. The preferred arylalkoxycarbonyl group is benzyloxycarbonyl.

The term "acyl" represents a hydrogen, $C_1$–$C_6$ alkyl, or aryl group attached to a carbonyl group. Typical acyl groups include formyl, acetyl, propionyl, butyryl, valeryl, benzoyl, and the like. The preferred acyl group is acetyl.

While all the formula II compounds of the present invention are believed to be useful in the synthesis of kainic acid, certain compounds of the invention are preferred for such use. Preferably, $R_4$ is acyl, alkoxycarbonyl, or arylalkoxycarbonyl, and $R_5$ is $C_1$–$C_6$ alkyl, aryl, or arylalkyl. More preferably, $R_4$ is alkoxycarbonyl or arylalkoxycarbonyl, and $R_5$ is $C_1$–$C_6$ alkyl or arylalkyl. Most preferably, $R_4$ is an arylalkoxycarbonyl group and $R_5$ is a $C_1$–$C_6$ alkyl group. The most preferred formula II compound for use in the synthesis of kainic acid is the compound wherein $R_4$ is benzyloxycarbonyl and $R_5$ is ethyl.

Similarly, while all the formula III compounds of the present invention are believed to be useful in the synthesis of kainic acid, certain compounds of the invention are preferred for such use. Preferably, $R_6$ is acyl, alkoxycarbonyl, or arylalkoxycarbonyl, and $R_7$ is $C_1$–$C_6$ alkyl, aryl, or arylalkyl. More preferably, $R_6$ is alkoxycarbonyl or arylalkoxycarbonyl, and $R_7$ is $C_1$–$C_6$ alkyl or arylalkyl. Most preferably, $R_6$ is an arylalkoxycarbonyl group and $R_7$ is a $C_1$–$C_6$ alkyl group. The most preferred formula III compound for use in the synthesis of kainic acid is the compound wherein $R_6$ is benzyloxycarbonyl and $R_7$ is ethyl.

While all the formula IV compounds of the present invention are believed to be useful in the synthesis of kainic acid, certain compounds of the invention are preferred for such use. Preferably, $R_8$ is acyl, alkoxycarbonyl, or arylalkoxycarbonyl, and $R_9$ is $C_1$–$C_6$ alkyl, aryl, or arylalkyl. More preferably, $R_8$ is alkoxycarbonyl or arylalkoxycarbonyl, and $R_9$ is $C_1$–$C_6$ alkyl or arylalkyl. Most preferably, $R_8$ is an arylalkoxycarbonyl group and $R_9$ is a $C_1$–$C_6$ alkyl group. The most preferred formula IV compound for use in the synthesis of kainic acid is the compound wherein $R_8$ is benzyloxycarbonyl and $R_9$ is ethyl.

While all the formula V compounds of the present invention are believed to be useful in the synthesis of kainic acid, certain compounds of the invention are preferred for such use. Preferably, $R_{10}$ is acyl, alkoxycarbonyl, or arylalkoxycarbonyl, and $R_{11}$ and $R_{12}$ are $C_1$–$C_6$ alkyl, aryl, or arylalkyl. More preferably, $R_{10}$ is alkoxycarbonyl or arylalkoxycarbonyl, and $R_{11}$ and $R_{12}$ are $C_1$–$C_6$ alkyl or arylalkyl. Most preferably, $R_{10}$ is an arylalkoxycarbonyl group and $R_{11}$ and $R_{12}$ are a $C_1$–$C_6$ alkyl group. The most preferred formula V compound for use in the synthesis of kainic acid is the compound wherein $R_{10}$ is benzyloxycarbonyl, $R_{11}$ is ethyl, and $R_{12}$ is methyl.

Similarly, while all the formula VIII compounds of the present invention are believed to be useful in the synthesis of kainic acid, certain compounds of the invention are preferred for such use. Preferably, $R_{15}$ is acyl, alkoxycarbonyl, or arylalkoxycarbonyl, and $R_{16}$ is $C_1$–$C_6$ alkyl, aryl, or arylalkyl. More preferably, $R_{15}$ is alkoxycarbonyl or arylalkoxycarbonyl, and $R_{16}$ is $C_1$–$C_6$ alkyl or arylalkyl. Most preferably, $R_{15}$ is an arylalkoxycarbonyl group and $R_{16}$ is a $C_1$–$C_6$ alkyl group. The most preferred formula VIII compound for use in the synthesis of kainic acid is the compound wherein $R_{15}$ is benzyloxycarbonyl and $R_{16}$ is ethyl.

While all the formula IX compounds of the present invention are believed to be useful in the synthesis of kainic acid, certain compounds of the invention are preferred for such use. Preferably, $R_{17}$ is acyl, alkoxycarbonyl, or arylalkoxycarbonyl, and $R_{18}$ is $C_1$–$C_6$ alkyl, aryl, or arylalkyl. More preferably, $R_{17}$ is alkoxycarbonyl or arylalkoxycarbonyl, and $R_{18}$ is $C_1$–$C_6$ alkyl or arylalkyl. Most preferably, $R_{17}$ is an arylalkoxycarbonyl group and $R_{18}$ is a $C_1$–$C_6$ alkyl group. The most preferred formula IX compound for use in the synthesis of kainic acid is the compound wherein $R_{17}$ is benzyloxycarbonyl and $R_{18}$ is ethyl.

The compounds of the present invention possess at least three asymmetric carbon atoms. These asymmetric centers are the substituted carbon atom bearing the carboxyl group (2) and the two adjacent carbon atoms (3 and 4). As such, the compounds can exist as a mixture of enantiomers or as a single enantiomer. The compounds of the present invention include not only the racemates, but also the respective enantiomers. The configuration of the preferred enantiomer for the compounds of the present invention is the same absolute stereochemistry as (–)-(2S,3S,4S)-kainic acid. This preferred relative and absolute stereochemistry is shown in the following formula:

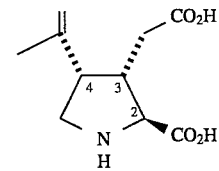

The compounds of the present invention are intermediates that are useful for the synthesis of kainic acid. The synthesis of kainic acid and the preparation of these intermediate compounds are shown in Scheme I.

Scheme I

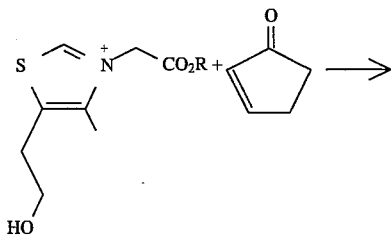

7

-continued
Scheme I

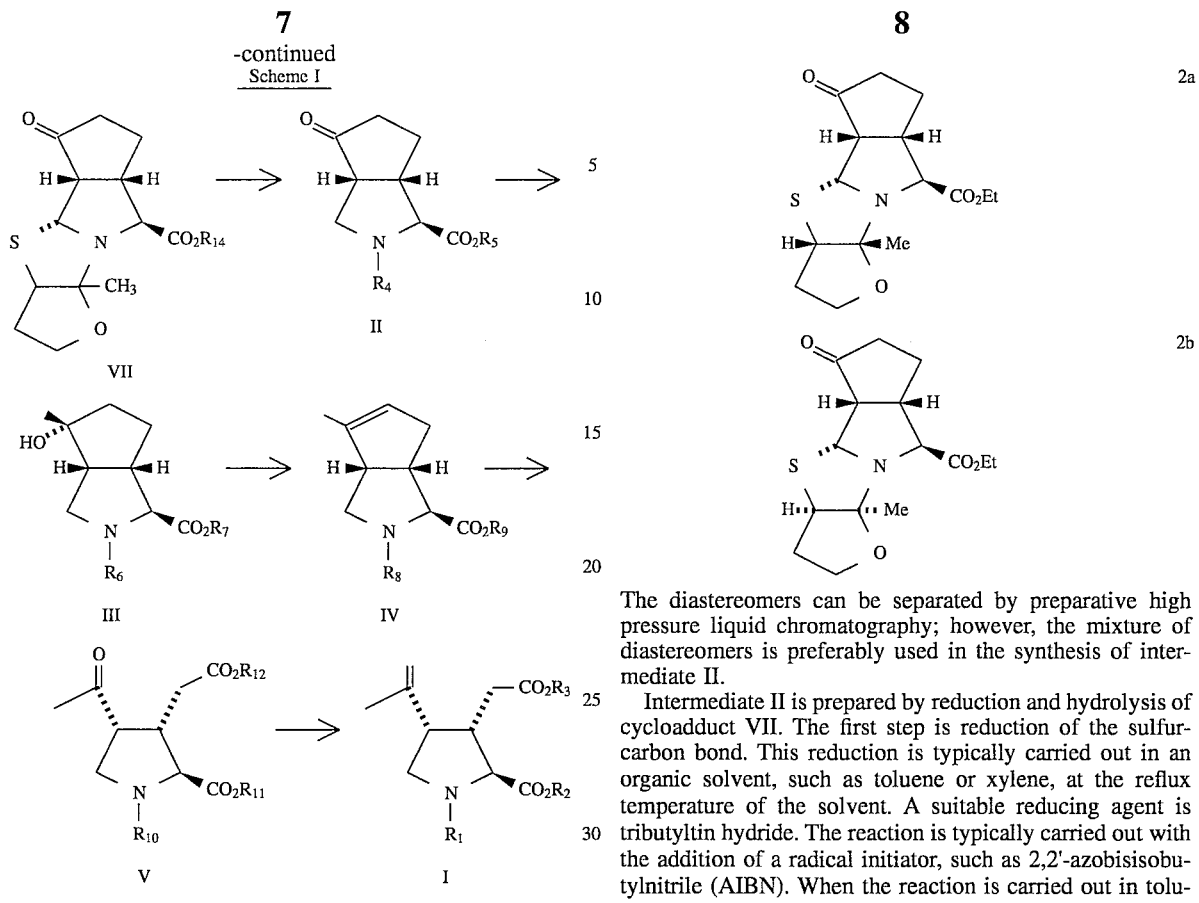

Generally, an azomethine ylid is reacted with cyclopentenone to produce cycloadduct VII. This cycloadduct is reduced and hydrolyzed to prepare bicyclic intermediate II. This bicyclic ketone is next methylated to prepare tertiary alcohol III. Dehydration of the alcohol intermediate III produces intermediate IV. Oxidation of this unsaturated intermediate leads to pyrrolidine intermediate V. This intermediate is then methylenated to convert the acetyl group to a propenyl group.

Intermediate VII is prepared by a 1,3-dipolar cycloaddition reaction between an azomethine ylid and 2-cyclopentene-1-one. This reaction is preferably carried out in a polar organic solvent, such as acetonitrile, in the presence of a tertiary amine base. Suitable tertiary amine bases for this reaction include triethylamine, N,N,-diisopropylethylamine, and 1,8-diazabicyclo[5.4.0]undec-7-ene (DBU). The reaction is typically carried out at a temperature of about 10° C. to about 50° C., preferably at room temperature. The preferred azomethine ylid for this cycloaddition reaction is one which readily reacts with the cyclopentenone, and does not readily decompose to lead to various reaction byproducts. The preferred azomethine ylid for this reaction is 3-(ethoxycarbonylmethyl)-5-(2-hydroxyethyl)-4-methylthiazolium bromide. The reaction is generally complete after about 2 hours.

Intermediate VII, prepared by the above route, exists as a mixture of diastereomers. The diastereomers exist in the relative configuration as shown below:

The diastereomers can be separated by preparative high pressure liquid chromatography; however, the mixture of diastereomers is preferably used in the synthesis of intermediate II.

Intermediate II is prepared by reduction and hydrolysis of cycloadduct VII. The first step is reduction of the sulfur-carbon bond. This reduction is typically carried out in an organic solvent, such as toluene or xylene, at the reflux temperature of the solvent. A suitable reducing agent is tributyltin hydride. The reaction is typically carried out with the addition of a radical initiator, such as 2,2'-azobisisobutylnitrile (AIBN). When the reaction is carried out in toluene, using tributyltin hydride as the reducing agent, the reaction is generally complete after about 6 hours.

The second step is hydrolysis of the reduced intermediate to produce intermediate II. This hydrolysis is carried out in a polar organic solvent, such as ether, or a water miscible organic solvent, such as ethanol, in the presence of an acid, preferably a catalytic amount of acid. Suitable acids for this hydrolysis include hydrochloric acid, sulfuric acid, sodium bisulfate, p-toluenesulfonic acid, trifluoroacetic acid, methanesulfonic acid, and trifluoromethanesulfonic acid; the preferred acid is dilute hydrochloric acid. The reaction is typically carried out at a temperature of about 10° to about 50° C., preferably at room temperature. When the reaction is carried out using a two-phase mixture comprising dilute hydrochloric acid and ether, the reaction is typically complete after about 14 hours.

Intermediate II is preferably protected on the ring nitrogen for further synthetic transformations. Methods for the protection of amino groups are generally described in McOmie, Protective Groups in Organic Chemistry, Plenum Press, N.Y., 1973 and Greene and Wutz, Protecting Groups in Organic Synthesis, 2d, ed., John Wiley & Sons, N.Y., 1991. The ring nitrogen may be protected with an acyl, alkoxycarbonyl, or an arylalkoxycarbonyl group. The preferred protecting groups are alkoxycarbonyl and arylalkoxycarbonyl groups. Most preferably, the protecting group is an arylalkoxycarbonyl group, such as benzyloxycarbonyl. The benzyloxycarbonyl protected intermediate II is prepared by the reaction of the formula II compound wherein $R_4$ is hydrogen with benzyl chloroformate. This reaction is carried out in a polar organic solvent, such as ethyl acetate, in the presence of a base. Suitable bases for this transformation include sodium hydroxide, triethylamine, N,N-diisopropylethylamine, potassium carbonate, and sodium bicarbonate; the preferred base is 50% sodium hydroxide. The reaction is typically carried out at a temperature of about 5° C. to about room temperature, preferably at 5° C.

Intermediate III is prepared by methylation of intermediate II. This reaction is carried in a polar organic solvent, such as methylene chloride. Suitable methylating reagents include a combination of titanium(IV) chloride and methyllithium. This reaction is typically carried out at a temperature of about −78° to about −50° C.

Intermediate III is dehydrated to produce intermediate IV. This dehydration is carried out using a protic acid, such as p-toluenesulfonic acid, or a Lewis acid, such as boron trifluoride etherate, as an acid catalyst. When boron trifluoride etherate is used, the reaction is carried out in a polar organic solvent, such as methylene chloride, at the reflux temperature of the solvent. When p-toluenesulfonic acid is used, the reaction is typically carried out in an organic solvent, such as toluene, at the reflux temperature of the solvent. The dehydration is generally complete after about 10 hours to about 18 hours.

Intermediate V is prepared by oxidation of intermediate IV. A suitable oxidizing agent for this transformation is prepared by the reaction of ruthenium(IV) oxide and sodium periodate or periodic acid or by the reaction of ruthenium(III) chloride and sodium periodate. When ruthenium(IV) oxide and sodium periodate are used to generate the oxidizing agent, the reaction is typically carried out in a mixture of one or more organic solvents and water. Suitable organic solvents include acetonitrile and carbon tetrachloride. When carried out at room temperature, the reaction is complete after about three hours.

Alternatively, intermediate V is prepared by oxidation of intermediate IV as shown in Scheme II.

Scheme II

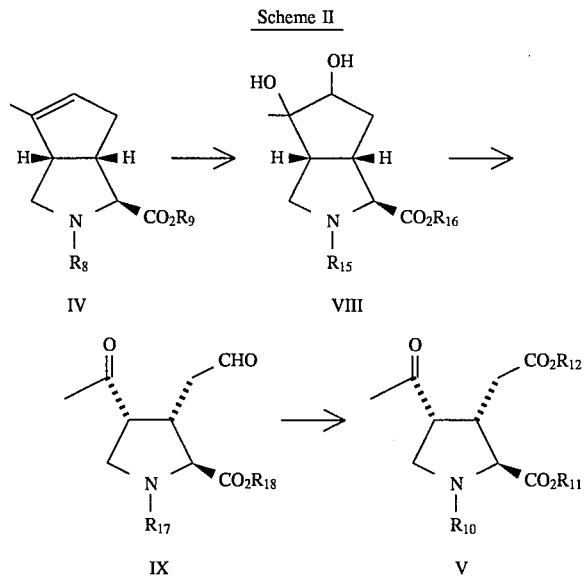

Generally, intermediate IV is oxidized to diol intermediate VIII. This compound is then further oxidized to keto-aldehyde intermediate IX. The aldehyde group of intermediate IX is then oxidized to a carboxyl group and esterified to prepare intermediate V.

Intermediate VIII is prepared by oxidation of intermediate IV. A suitable oxidizing agent for this transformation is a mixture of osmium tetroxide and N-methylmorpholine-N-oxide. The reaction is typically carried out in a mixture of a water miscible organic solvent, such as acetone, and water. When carried out at room temperature, the reaction is generally complete after about 12 to about 24 hours.

Intermediate VIII is then further oxidized to produce keto-aldehyde intermediate IX. A suitable oxidizing agent for this transformation is sodium periodate or periodic acid; preferably sodium periodate. The reaction is typically carried out in a polar organic solvent, such as metrahydrofuran, or in a mixture of a polar organic solvent and water, such as tetrahydrofuran and water. When carried out at room temperature, the reaction is complete after about three hours.

The aldehyde group is converted to a carboxyl group to produce intermediate V. A suitable oxidizing agent for this transformation is potassium permanganate. The oxidation is typically carried out in a mixture of a water miscible organic solvent, such as t-butanol, and water. The solution may be buffered by the addition of a buffering agent, such as monobasic sodium phosphate. When the reaction is carried out at room temperature, the reaction is generally complete after about 3 hours.

Alternatively, intermediate IV can be directly oxidized to intermediate IX. A suitable oxidizing agent for this transformation is ozone. The reaction is carried out in a polar organic solvent, such methylene chloride, at a temperature of about −78° C. to about −50° C., preferably at −78° C. After the addition of ozone, the reaction mixture is treated with dimethyl sulfide and allowed to slowly warm to room temperature. The reaction is generally complete after about 18 hours.

The product of the oxidation is preferably protected on the free carboxyl group for further chemical transformation. Methods for the protection of carboxyl groups are generally described in McOmie, Protective Groups in Organic Chemistry, Plenum Press, N.Y., 1973 and Greene and Wutz, Protecting Groups in Organic Synthesis, 2d, ed., John Wiley & Sons, N.Y., 1991. The carboxyl group may be protected as the $C_1$–$C_6$ alkyl, aryl, or arylalkyl ester. The preferred ester is the $C_1$–$C_6$ alkyl ester; the methyl ester is the most preferred. This ester is prepared by the reaction of intermediate V, wherein $R_{12}$ is hydrogen, with iodomethane in the presence of cesium carbonate. This reaction is typically carried out in a polar organic solvent, such as dimethylformamide. The reaction is generally complete after about 1 hour at room temperature.

Intermediate V is methylenated to produce a compound of formula I. A suitable methylenating reagent is a mixture of diiodomethane, zinc, and titanium(IV) chloride. This reaction is carried out in a polar organic solvent, such as tetrahydrofuran, at a temperature of about 15° C. to about 50° C., preferably at room temperature. The reaction is generally complete after about 12 hours to about 18 hours.

Deprotection of the compound produced by the above scheme affords kainic acid. A suitable method for deprotecting the formula I compounds, wherein $R_1$, $R_2$, and $R_3$ are other than hydrogen, is the use of sodium hydroxide. This reaction is typically carried out in 2.5N sodium hydroxide at reflux. After a period of about four days, kainic acid is isolated from the reaction using standard isolation techniques as exemplified herein.

The process described above produces kainic acid and the intermediate formula I–VI, VIII, and IX compounds in racemic form. The enantiomers of (±)-kainic acid, as well as the enantiomers of the racemic intermediate compounds, are resolved using standard resolution techniques. See Jacques, Collet, and Wilen, Enantiomers, Racemates, and Resolutions, John Wiley and Sons, N.Y., 1981. The preferred method for the resolution of these enantiomers is the formation of diastereomeric salts between the racemic substances and optically-active (chiral) resolving agents. See, Jacques, Collet, and wilen, Enantiomers, Racemates, and Resolutions, Chapter 5. The present compounds can be resolved using either acidic or basic chiral resolving agents. Examples of suitable acidic chiral resolving agents include (+)-camphoric acid, (−)-dibenzoyltartaric acid, diacetoneketogulonic acid, (+) and (−)-mandelic acid, (−)-malic acid, (+) and (−)-quinic acid, and (+) and (−)-tartaric acid. Examples of suitable basic chiral resolving agents include brucine, cinchonidine, cinchonine, strychnine, (+) and (−)-ephedrine, (−)-2-amino-1-butanol, (+) and (−)-α-methylbenzylamine, (+)-amphetamine, and (+)-deoxyephedrine. The resolution of (±)-kainic acid with (+)-ephedrine, which has been described previously, is typical of such resolutions. Oppolzer and Andres, *Helvetica Chimica Acta*, 62, 2282, (1979).

The following compounds illustrate the compounds of the present invention and the compounds of the examples. These compounds are illustrative only, and should not be construed as limiting the present invention.

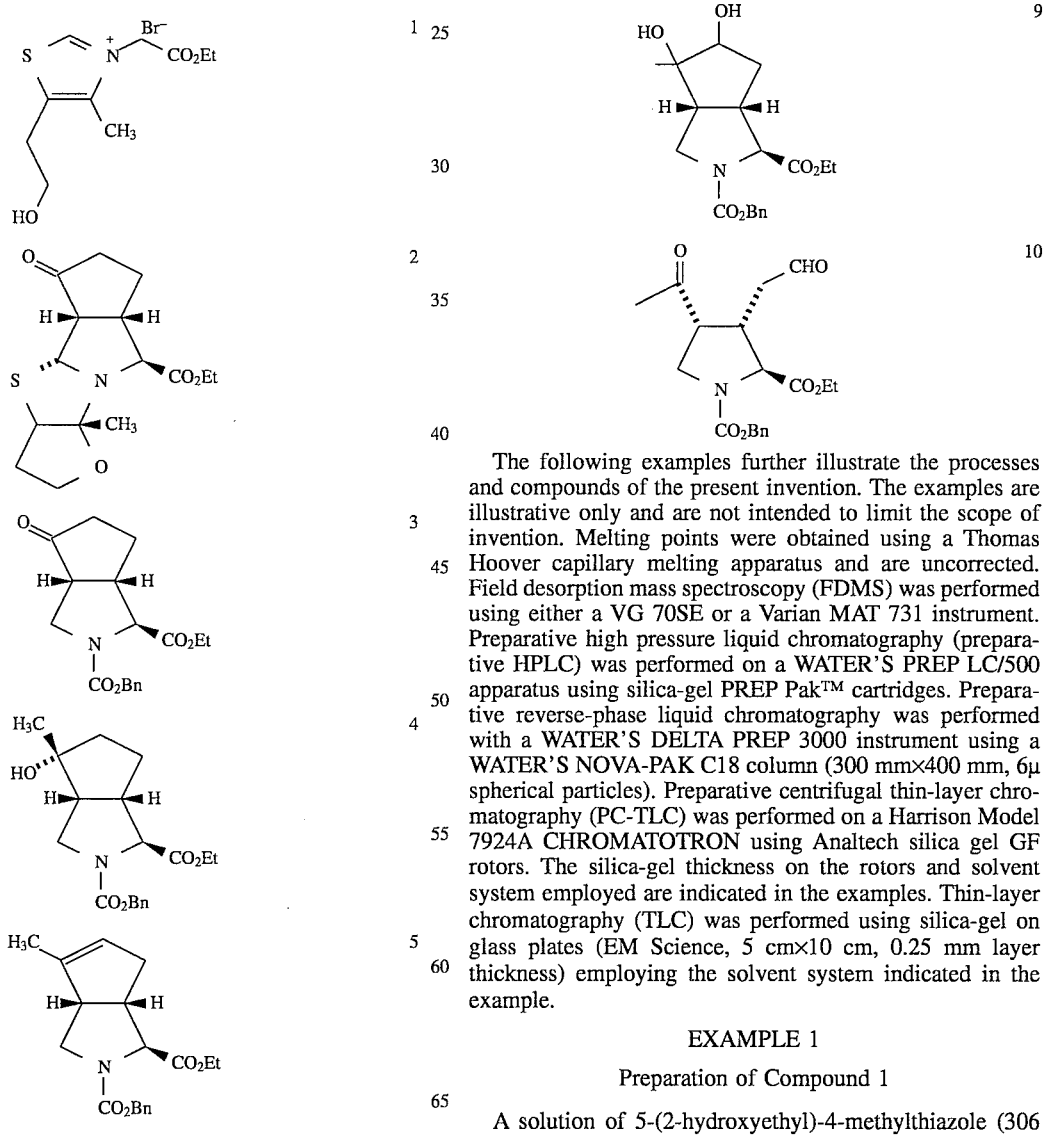

The following examples further illustrate the processes and compounds of the present invention. The examples are illustrative only and are not intended to limit the scope of invention. Melting points were obtained using a Thomas Hoover capillary melting apparatus and are uncorrected. Field desorption mass spectroscopy (FDMS) was performed using either a VG 70SE or a Varian MAT 731 instrument. Preparative high pressure liquid chromatography (preparative HPLC) was performed on a WATER'S PREP LC/500 apparatus using silica-gel PREP Pak™ cartridges. Preparative reverse-phase liquid chromatography was performed with a WATER'S DELTA PREP 3000 instrument using a WATER'S NOVA-PAK C18 column (300 mm×400 mm, 6μ spherical particles). Preparative centrifugal thin-layer chromatography (PC-TLC) was performed on a Harrison Model 7924A CHROMATOTRON using Analtech silica gel GF rotors. The silica-gel thickness on the rotors and solvent system employed are indicated in the examples. Thin-layer chromatography (TLC) was performed using silica-gel on glass plates (EM Science, 5 cm×10 cm, 0.25 mm layer thickness) employing the solvent system indicated in the example.

EXAMPLE 1

Preparation of Compound 1

A solution of 5-(2-hydroxyethyl)-4-methylthiazole (306 g) and ethyl bromoacetate (356.2 g) in ethanol (1 L) was heated to reflux. After two hours, the ethanol was removed by distillation and the residue treated with isopropanol (1.5 L). The resulting solution was cooled to about 0° C., causing crystallization of compound 1. After three hours, the crystalline material was separated from the mother liquor, and additional crystals obtained by prolonged cooling of the mother liquor at 0° C. Combination of the crystalline material gave 474.3 g of compound 1.

Melting point 96°–96° C.

FDMS: m/z=230 (M$^+$-Br).

Analysis calculated for $C_{10}H_{16}BrNO_3S$: C, 38.72; H, 5.20; N, 4.52. Found: C, 38.64; H, 5.04; N, 4.47.

EXAMPLE 2

Preparation of Compounds 2a and 2b

A mixture of the compound from Example 1 (20 g) and 2-cyclopenten-1-one (25.0 g) in acetonitrile (30 ml) was treated with triethylamine (7.17 g). The resulting mixture was stirred at room temperature under a nitrogen atmosphere. After 24 hours, the reaction mixture was diluted with ether (200 ml) and brine (200 ml). The phases were separated and the aqueous phase was extracted with ether (3×200 ml). The organic phases were combined, washed with brine (200 ml), dried over potassium carbonate, and concentrated in vacuo to a dark oil. This oil was purified by preparative HPLC, eluting with a linear gradient of hexane/ethyl acetate (4:1) to hexane/ethyl acetate (1:1), to give two diastereomeric products. The first diastereomeric compound 2a (13.6 g), and the second diastereomeric compound 2b (1.98 g), were combined for use in the next step.

Compound 2a.

Melting point 70°–74° C.

FDMS: m/z=311 (M$^+$).

Analysis calculated for $C_{15}H_{21}NO_4S$: C, 57.86; H, 6.80; N, 4.50. Found: C, 57.63; H, 6.87; N, 4.29.

Compound 2b.

Melting point 126°–128° C.

FDMS: m/z=311 (M$^+$).

Analysis calculated for $C_{15}H_{21}NO_4S$: C, 57.86; H, 6.80; N, 4.50. Found: C, 57.56; H, 6.86; N, 4.33.

EXAMPLE 3

Preparation of Compound 3

A solution of the diastereomeric compounds prepared as described in Example 2 (311 g), 2,2'-azobisisobutylnitrile (24.6 g), and tributyltin hydride (360 ml) in toluene (1.6 L) was heated to reflux under a nitrogen atmosphere. After six hours, the volatiles were removed by distillation. The residue was treated with ether (1 L) and 1N hydrochloric acid (1.1 L), and the resulting two-phase mixture vigorously stirred at room temperature. After 14 hours, the organic phase was removed, and the aqueous phase extracted with ether (10×1 L). The aqueous phase was then cooled to 5° C. and sequentially treated with ethyl acetate (1 L) and benzyl chloroformate (190 g). The resulting solution was vigorously stirred and treated with 50% sodium hydroxide (170 ml). After the addition of sodium hydroxide was complete, the reaction mixture was allowed to warm to room temperature. After one hour at room temperature, the organic phase was removed and the aqueous phase extracted with ethyl acetate (4×1 L). The combined organic phase was washed with water (1 L), dried over magnesium sulfate, and concentrated in vacuo to a red oil. This oil was purified by preparative HPLC, eluting with a linear gradient of hexane/ethyl acetate (4:1) to hexane/ethyl acetate (1:1), to give 212.8 g of compound 3 as a white solid. Melting 66°–68° C.

FDMS: m/z=331 (M$^+$).

Analysis calculated for $C_{18}H_{21}NO_5$: C, 65.24; H, 6.39; N, 4.23. Found: C, 64.95; H, 6.39; N, 4.27.

EXAMPLE 4

Preparation of Compound 4

A mixture of ether (100 ml) and methylene chloride (100 ml) was cooled to –78° C. under a nitrogen atmosphere. The cold mixture was sequentially treated with titanium(IV) chloride (45.3 ml, 1M solution in methylene chloride) and methyllithium (32.3 ml, 1.4M solution in ether). The resulting dark solution was stirred at –78° C. for 30 minutes, then allowed to warm slowly to –50° C. This dark solution was treated with a solution of the compound from Example 3 (10.0 g) in methylene chloride (50 ml). Upon completion of the addition of Compound 3, the reaction mixture was allowed to warm slowly to 0° C. After two hours, the reaction mixture was added to a mixture of ether (300 ml) and water (300 ml). The organic phase was removed and the aqueous phase was extracted with ether (2×100 ml). The combined organic phase was washed with water (200 ml) and brine (200 ml), dried over magnesium sulfate, and concentrated in vacuo to a pale yellow oil. This oil was purified by preparative HPLC, eluting with a linear gradient of hexane/ethyl acetate (7:1) to hexane/ethyl acetate (1:1), to give 9.12 g of compound 4 as a colorless oil.

FDMS: m/z=347 (M$^+$).

Analysis calculated for $C_{19}H_{25}NO_5$: C, 65.69; H, 7.25; N, 4.03. Found: C, 65.78; H, 7.33; N, 4.08.

EXAMPLE 5

Preparation of Compound 5

Method A

A solution of the compound from Example 4 (8.40 g) in methylene chloride (75 ml) was treated with boron trifluoride etherate (5.0 ml) and the resulting solution heated to reflux under a nitrogen atmosphere. After 16 hours, the reaction solution was allowed to cool to room temperature. This solution was added to a mixture of ether (200 ml) and water (200 ml). The organic phase was removed and the aqueous phase was extracted with ether (3×100 ml). The combined organic phase was washed with water until the pH of the aqueous wash was about pH 7.0. The organic phase was then dried over magnesium sulfate and concentrated in vacuo to give 7.45 g of compound 5 as a pale yellow oil. This material was used in the next step without further purification.

FDMS: m/z=329 (M$^+$).

Analysis calculated for $C_{19}H_{23}NO_4$: C, 69.28; H, 7.04; N, 4.25. Found: C, 69.51; H, 6.99; N, 4.15.

Method B

A solution of the compound from Example 4 (8.37 g) in toluene (150 ml) was treated with p-toluenesulfonic acid (1.0 g) and the resulting solution heated to reflux. After eighteen hours, the reaction solution was allowed to cool to room temperature. This solution was added to a mixture of ether (200 ml) and 1N sodium hydroxide (200 ml). The organic phase was removed and the aqueous phase was extracted with ether (3×100 ml). The combined organic phase was washed with water (200 ml) and brine (200 ml), dried over magnesium sulfate, and concentrated in vacuo to a dark yellow oil. This material was purified by preparative HPLC, eluting with hexane/ethyl acetate (4:1), to give 5.86 g of compound 5.

EXAMPLE 6

Preparation of Compound 6

A mixture of ruthenium(IV) oxide hydrate (0.45 g), sodium periodate (14.9 g), acetonitrile (30 ml), carbon tetrachloride (30 ml), and water (45 ml) was vigorously stirred at room temperature. After 15 minutes, this mixture was treated with a solution of the compound prepared as described in Example 5 (5.62 g) in acetonitrile (5 ml) and carbon tetrachloride (5 ml). The resulting dark mixture was vigorously stirred at room temperature. After four hours, the reaction mixture was added to a mixture of ether (100 ml) and water (100 ml). The organic phase was removed and the aqueous phase was extracted with ether (2×100 ml). The combined organic phase was washed with water (2×100 ml), dried over magnesium sulfate, and concentrated in vacuo. The residue was added to dimethylformamide (50 ml). The resulting solution was sequentially treated with potassium carbonate (3.6 g) and iodomethane (4.85 g). After three hours at room temperature under a nitrogen atmosphere, the reaction mixture was partitioned between ether (300 ml) and 1N hydrochloric acid (300 ml). The organic layer was removed and the aqueous layer was extracted with ether (3×200 ml). The combined organic phase was washed with water (500 ml), dried over magnesium sulfate, and concentrated in vacuo to give a pale yellow oil. This oil was purified by preparative reverse-phase HPLC (200 mg per run), eluting with 45% acetonitrile/H$_2$O. The fractions containing pure compound 6 were combined and extracted with ether. The ether extracts were dried over MgSO$_4$ and concentrated in vacuo to give 3.40 g of compound 6 as a waxy white solid. Melting point 55°–57° C.

FDMS: m/z=391 (M$^+$).

Analysis calculated for C$_{20}$H$_{25}$NO$_7$: C, 61.37; H, 6.44; N, 3.58. Found: C, 61.60; H, 6.68; N, 3.66.

EXAMPLE 7

Preparation of Compound 7

A suspension of zinc (3.0 g) and diiodomethane (2.06 ml) in tetrahydrofuran (80 ml) was treated with titanium(IV) chloride (5.6 ml, 1.0M solution in methylene chloride). The resulting black mixture was stirred at room temperature under a nitrogen atmosphere. After one hour, this dark mixture was treated with a solution of the compound from Example 6 (2.0 g) in methylene chloride (5 ml). After 16 hours at room temperature under a nitrogen atmosphere, the reaction mixture was added to a mixture of ether (200 ml) and 0.5N hydrochloric acid (200 ml). The organic phase was removed and the aqueous phase was extracted with ether (3×200 ml). The combined organic phases was washed with water (200 ml) and brine (200 ml), dried over magnesium sulfate, and concentrated in vacuo to a yellow oil. This oil was purified by PC-TLC (4 mm silica gel thickness), eluting with a gradient of hexane/ethyl acetate (9:1) to hexane/ethyl acetate (4:1) to give 0.82 g of compound 7 as a colorless oil.

FDMS: m/z=389 (M$^+$).

Analysis calculated for C$_{21}$H$_{27}$NO$_6$: C, 64.77; H, 6.99; N, 3.60. Found: C, 64.99; H, 7.17; N, 3.50.

EXAMPLE 8

Preparation of Compound 8

A mixture of the compound from Example 7 (0.64 g) and 2.5N sodium hydroxide (10 ml) was heated to reflux. After four days, the pH was adjusted to pH 2 by the addition of 1N hydrochloric acid. The resulting precipitate was removed by filtration. The filtrate was subjected to cation exchange chromatography on DOWEX 50XB-100, eluting with 10% pyridine/water. The fractions containing compound 8 were combined and concentrated to in vacuo to give 0.33 g of compound 8 as a white solid. Melting point 243°–245° C. (dec).

FDMS: m/z=213 (M$^+$).

Analysis calculated for C$_{10}$H$_{15}$NO$_4$: C, 56.33; H, 7.09; N, 6.57. Found: C, 56.39; H, 7.34; N, 6.54.

EXAMPLE 9

Preparation of Compound 9

A mixture of the compound from Example 5 (3.3 g) and N-methylmorpholine-N-oxide (3.0 g) in acetone (125 ml) and water (35 ml) was treated with osmium tetroxide (1–10 mg). After sixteen hours at room temperature, the reaction mixture was added to a mixture of ether (200 ml) and water (200 ml). The organic phase was removed and the aqueous phase was extracted with ether (3×100 ml). The combined organic phase was washed with water (200 ml), dried over magnesium sulfate, and concentrated in vacuo to a light brown oil. This oil was purified by PC-TLC (4 mm silica-gel rotor), eluting with a linear gradient of hexane/ethyl acetate (9:1) to hexane/ethyl acetate (1:2), to give 3.58 g of compound 9 as a colorless oil.

FDMS: m/z=363 (M$^+$).

Analysis calculated for C$_{19}$H$_{25}$NO$_6$: C, 62.80; H, 6.93; N, 3.85. Found: C, 62.68; H, 6.82; N, 3.55.

EXAMPLE 10

Preparation of Compound 10

A solution of the compound from Example 9 (3.5 g) in tetrahydrofuran (60 ml) was treated with a solution of sodium periodate (3.1 g) in water (40 ml). After three hours at room temperature, the reaction mixture was added to a mixture of ether (100 ml) and water (100 ml). The organic phase was separated and the aqueous phase was extracted with ether (3×100 ml). The combined organic phase was washed with water (100 ml), dried over magnesium sulfate, and concentrated in vacuo to give 3.43 g of compound 10 as a colorless oil.

FDMS: m/z=361 (M$^+$).

Analysis calculated for C$_{19}$H$_{23}$NO$_6$: C, 63.15; H, 6.41; N, 3.88. Found: C, 63.10; H, 6.57; N, 3.87.

EXAMPLE 11

Preparation of Compound 10

A solution of the compound from Example 5 (3.30 g) in methylene chloride (125 ml) was cooled to −78° C. and treated with ozone until the solution remained blue in color. The reaction was purged with nitrogen until the excess ozone was removed, treated with dimethyl sulfide (7.35 ml), and allowed to slowly warm to room temperature. After 18 hours, the volatiles were removed under reduced pressure. The residue was purified by preparative HPLC, eluting with a gradient of hexane/ethyl acetate (9:1) to hexane/ethyl acetate (1:1), to give 2.01 g of compound 10 as a colorless oil.

EXAMPLE 12

Preparation of Compound 6

A solution of the compound prepared as described in Example 10 (4.46 g) in t-butyl alcohol (25 ml) was treated sequentially with a 5% aqueous solution of monobasic sodium phosphate (25 ml) and 1M potassium permanganate (13.5 ml). After three hours, the reaction mixture was added to a mixture of saturated sodium sulfite (100 ml) and ether (200 ml) and the aqueous acidified with 2M sodium bisulfate to pH 2. The organic phase was removed and the aqueous phase extracted with ether (3×100 ml). The combined organic phase was washed with water until the aqueous extract were neutral, dried over magnesium sulfate, and concentrated in vacuo to a light yellow oil. This oil was dissolved in dimethyl formamide (50 ml) and treated with potassium carbonate (13.8 g) and iodomethane (5.2 g). After 30 hours at room temperature, the reaction mixture was added to a mixture of ether (200 ml) and 1N hydrochloric acid (200 ml). The organic phase was removed and the aqueous phase extracted with ether (3×100 ml). The combined organic phase was dried over magnesium sulfate and concentrated in vacuo to 3.0 g of a yellow oil. This oil was purified by preparative reverse-phase HPLC, as described in Example 6, to give 1.78 g of compound 6.

I claim:

1. A compound of the formula

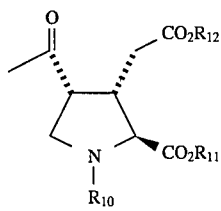

V wherein $R_{10}$ is hydrogen, acyl, alkoxycarbonyl, or arylalkoxycarbonyl;

$R_{11}$ is hydrogen, $C_1$–$C_6$ alkyl, aryl, or arylalkyl; and $R_{12}$ is hydrogen, $C_1$–$C_6$ alkyl, aryl, or arylalkyl;

provided that $R_{10}$, $R_{11}$, and $R_{12}$ are not all hydrogen.

2. The compound of claim 1 wherein $R_{10}$ is acyl, alkoxycarbonyl or arylalkoxycarbonyl.

3. The compound of claim 1 wherein $R_{10}$ is alkoxycarbonyl or arylalkoxycarbonyl.

4. The compound of claim 3 wherein $R_{11}$ is hydrogen, $C_1$–$C_6$ alkyl, or arylalkyl, and $R_{12}$ is hydrogen, $C_1$–$C_6$ alkyl, or arylalkoxycarbonyl.

5. The compound of claim 3 wherein $R_{11}$ is hydrogen or $C_1$–$C_6$ alkyl and $R_{12}$ is hydrogen or $C_1$–$C_6$ alkyl.

6. The compound of claim 5 wherein $R_{10}$ is benzyloxycarbonyl, $R_{11}$ is ethyl, and $R_{12}$ is methyl.

7. A compound of the formula

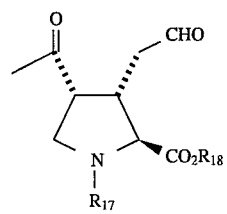

IX wherein $R_{17}$ is hydrogen, acyl, alkoxycarbonyl, or arylalkoxycarbonyl; and $R_{18}$ is hydrogen, $C_1$–$C_6$ alkyl, aryl, or arylalkyl.

8. The compound of claim 7 wherein $R_{17}$ is alkoxycarbonyl or arylalkoxycarbonyl, and $R_{18}$ is $C_1$–$C_6$ alkyl, aryl, or arylalkyl.

9. The compound of claim 8 wherein $R_{17}$ is arylalkoxycarbonyl and $R_{18}$ is $C_1$–$C_6$ alkyl.

10. The compound of claim 9 wherein $R_{17}$ is benzyloxycarbonyl and $R_{18}$ is ethyl.

11. The compound of claim 7 wherein $R_{17}$ is hydrogen and $R_{18}$ is hydrogen.

12. A process for preparing a compound of the formula

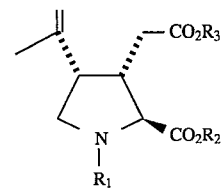

I wherein $R_1$ is acyl, alkoxycarbonyl, or arylalkoxycarbonyl;

$R_2$ is $C_1$–$C_6$ alkyl, aryl, or arylalkyl; and $R_3$ is $C_1$–$C_6$ alkyl, aryl, or arylalkyl;

which comprises the steps of:

(1) methylating a compound of the formula

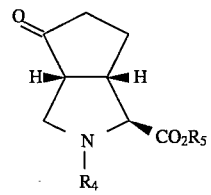

II wherein $R_4$ is acyl, alkoxycarbonyl, or arylalkoxycarbonyl; and $R_5$ is $C_1$–$C_6$ alkyl, aryl, or arylalkyl;

with a methylating reagent to produce a compound of the formula

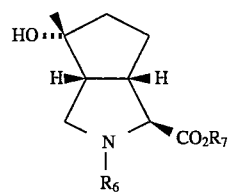

III wherein $R_6$ is acyl, alkoxycarbonyl, or arylalkoxycarbonyl; and $R_7$ is $C_1$–$C_6$ alkyl, aryl, or arylalkyl;

(2) dehydrating said formula III compound to produce a compound of the formula

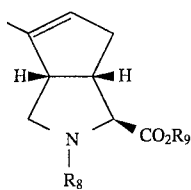

wherein $R_8$ is acyl, alkoxycarbonyl, or arylalkoxycarbonyl; and $R_9$ is $C_1$–$C_6$ alkyl, aryl, or arylalkyl;

(3) oxidizing said formula IV compound to produce a compound of the formula

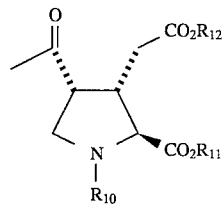

wherein $R_{10}$ is acyl, alkoxycarbonyl, or arylalkoxycarbonyl;

$R_{11}$ is $C_1$–$C_6$ alkyl, aryl, or arylalkyl; and $R_{12}$ is hydrogen;

(4) esterifying said formula V compound to produce a compound of formula V wherein $R_{10}$ is acyl, alkoxycarbonyl, or arylalkoxycarbonyl;

$R_{11}$ is $C_1$–$C_6$ alkyl, aryl, or arylalkyl; and $R_{12}$ is $C_1$–$C_6$ alkyl, aryl, or arylalkyl; and (5) methylenating said formula V compound.

13. The process of claim 12 wherein the methylating reagent is methyllithium and titanium(IV) chloride.

14. The process of claim 12 wherein the formula III compound is dehydrated with boron trifluoride etherate.

15. The process of claim 12 wherein the formula III compound is dehydrated with p-toluenesulfonic acid.

16. The process of claim 12 wherein the formula IV compound is oxidized with ruthenium(IV) oxide and sodium periodate.

17. The process of claim 12 wherein the formula V compound is methylenated with diiodomethane, zinc, and titanium(IV) chloride.

18. A process for preparing a compound of the formula

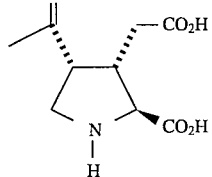

which comprises the steps of claim 12 and the additional step of hydrolyzing a compound of the formula

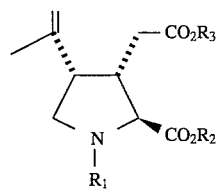

wherein $R_1$ is acyl, alkoxycarbonyl, or arylalkoxycarbonyl;

$R_2$ is $C_1$–$C_6$ alkyl, aryl, or arylalkyl; and $R_3$ is $C_1$–$C_6$ alkyl, aryl, or arylalkyl.

19. The process of claim 18 wherein the formula I compound is hydrolyzed with sodium hydroxide.

20. The process of claim 12 wherein said oxidation step comprises the steps of:

(1) oxidizing a compound of the formula

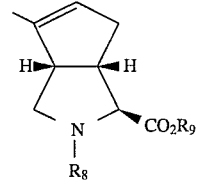

wherein $R_8$ is acyl, alkoxycarbonyl, or arylalkoxycarbonyl; and $R_9$ is $C_1$–$C_6$ alkyl, aryl, or arylalkyl to produce a compound of the formula

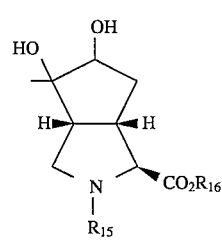

wherein $R_{15}$ is acyl, alkoxycarbonyl, or arylalkoxycarbonyl; and $R_{16}$ is $C_1$–$C_6$ alkyl, aryl, or arylalkyl;

(2) oxidizing said formula VIII compound to produce a compound of the formula

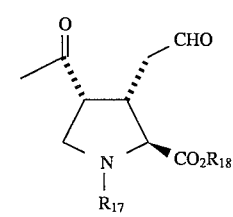

wherein $R_{17}$ is acyl, alkoxycarbonyl, or arylalkoxycarbonyl;

$R_{18}$ is $C_1$–$C_6$ alkyl, aryl, or arylalkyl; and (3) oxidizing said formula IX compound to produce a compound of the formula

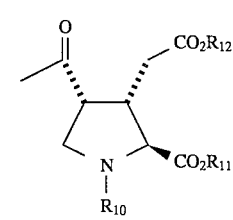

wherein $R_{10}$ is acyl, alkoxycarbonyl, or arylalkoxycarbonyl;

$R_{11}$ is $C_1$–$C_6$ alkyl, aryl, or arylalkyl; and $R_{12}$ is hydrogen.

21. The process of claim 12 wherein said oxidation step comprises the steps of:

(1) oxidizing a compound of the formula

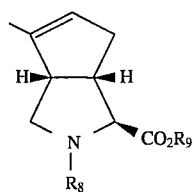 IV wherein
 $R_8$ is acyl, alkoxycarbonyl, or arylalkoxycarbonyl; and
 $R_9$ is $C_1$–$C_6$ alkyl, aryl, or arylalkyl to produce a compound of the formula

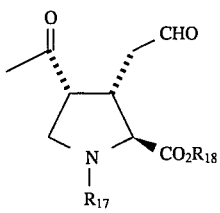 IX wherein
 $R_{17}$ is acyl, alkoxycarbonyl, or arylalkoxycarbonyl;
 $R_{18}$ is $C_1$–$C_6$ alkyl, aryl, or arylalkyl; and
(2) oxidizing said formula IX compound to produce a compound of the formula

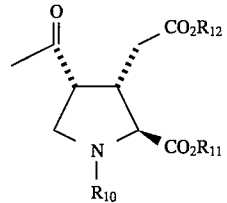 V wherein
 $R_{10}$ is acyl, alkoxycarbonyl, or arylalkoxycarbonyl;
 $R_{11}$ is $C_1$–$C_6$ alkyl, aryl, or arylalkyl; and
 $R_{12}$ is hydrogen.

* * * * *